(12) United States Patent
Lambert et al.

(10) Patent No.: US 6,399,841 B1
(45) Date of Patent: Jun. 4, 2002

(54) METHOD FOR SEPARATING HYDROGEN FLUORIDE FROM ITS MIXTURES WITH 1,1,1,3,3-PENTAFLUOROBUTANE AND METHOD FOR MAKING 1,1,1,3,3-PENTAFLUOROBUTANE

(75) Inventors: Alain Lambert, Beauvechain; Vincent Wilmet, Louvain-la-Neuve, both of (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/937,389
(22) PCT Filed: Mar. 15, 2000
(86) PCT No.: PCT/EP00/02282
§ 371 (c)(1),
(2), (4) Date: Sep. 24, 2001
(87) PCT Pub. No.: WO00/56687
PCT Pub. Date: Sep. 28, 2000

(30) Foreign Application Priority Data

Mar. 24, 1999 (FR) ............................................. 99 03917
Jul. 15, 1999 (FR) ............................................. 99 09220

(51) Int. Cl.$^7$ .......................... C07C 17/38; C07C 17/00
(52) U.S. Cl. ....................... 570/180; 570/177; 570/164; 570/165
(58) Field of Search ................................. 570/177, 180, 570/164, 165

(56) References Cited

U.S. PATENT DOCUMENTS

| 5,208,398 A | 5/1993 | Wismer |
| 5,739,406 A | 4/1998 | Pennetreau et al. |
| 2001/0004961 A1 | 6/2001 | Herkelmann et al. |

*Primary Examiner*—Alan Siegel
(74) *Attorney, Agent, or Firm*—Connolly Bove Lodge & Hutz LLP

(57) ABSTRACT

Hydrogen fluoride is separated from its mixtures with 1,1,1,3,3-pentafluorobutane by extraction using an organic solvent containing a 1,1,1,3,3-chloro(fluoro)butane.

13 Claims, No Drawings

METHOD FOR SEPARATING HYDROGEN FLUORIDE FROM ITS MIXTURES WITH 1,1,1,3,3-PENTAFLUOROBUTANE AND METHOD FOR MAKING 1,1,1,3,3-PENTAFLUOROBUTANE

This application is a 371 of PCT/EP00/02282 filed Mar. 15, 2000.

The present invention relates to a process for the separation of hydrogen fluoride from its mixtures with 1,1,1,3,3-pentafluorobutane.

1,1,1,3,3-Pentafluorobutane (HFC-365mfc) may be prepared by the reaction of an appropriate chlorinated precursor with hydrogen fluoride, as described for example in Patent Application EP-A1-0699649 in the name of SOLVAY. In such a process, at the outlet of a hydrofluorination reactor, the mixture of reaction products contains, in addition to the desired 1,1,1,3,3-pentafluorobutane, hydrogen chloride resulting from the elimination of the chlorine atom(s) from the starting chlorinated precursor, hydrogen fluoride and, optionally, inert diluents and various intermediates or by-products in small quantities. Given that an excess of hydrogen fluoride relative to the chlorinated precursor is normally used, unconverted hydrogen fluoride often remains in the mixture of reaction products. While most of the constituents of the mixture of reaction products can be easily completely separated by distillation, complete separation between hydrogen fluoride and 1,1,1,3,3-pentafluorobutane is very difficult to carry out by distillation. It has indeed been observed that these compounds form an azeotropic mixture.

The object of the present invention is to provide an efficient process for the separation of hydrogen fluoride from its mixtures with 1,1,1,3,3-pentafluorobutane.

To this effect, the invention relates to a process for the separation of hydrogen fluoride from its mixtures with 1,1,1,3,3-pentafluorobutane, according to which the separation is carried out by extraction using at least one organic solvent containing at least one chloro(fluoro)butane of general formula

$$CCl_aF_{3-a}CH_2CCl_bF_{2-b}CH_3 \quad (I)$$

with a an integer from 0 to 3, b an integer from 0 to 2, the sum of a and b being at least equal to 1.

Preferably, the organic solvent contains 1,1,1,3,3-pentachlorobutane $CCl_3$—$CH_2$—$CCl_2$—$CH_3$, a chlorofluorobutane of formula $CCl_2F$—$CH_2$—$CCl_2$—$CH_3$, $CClF_2$—$CH_2$—$CCl_2$—$CH_3$, $CF_3$—$CH_2$—$CCl_2$—$CH_3$, $CF_3$—$CH_2$—$CClF$—$CH_3$, $CCl_2F$—$CH_2$—$CClF$—$CH_3$, $CClF_2$—$CH_2$—$CClF$—$CH_3$ and $CClF_2$—$CH_2$—$CF_2$—$CH_3$, $CCl_3$—$CH_2$—$CClF$—$CH_3$, $CCl_3$—$CH_2$—$CF_2$—$CH_3$, $CCl_2F$—$CH_2$—$CF_2$—$CH_3$, or a mixture of these compounds. In a particularly preferred manner, the organic solvent contains 1,1,1,3,3-pentachlorobutane.

The organic solvent may contain other halogenated or nonhalogenated compounds.

By way of example of a nonhalogenated compound which may be possibly present in the organic solvent, there may be mentioned hydrocarbons containing from 5 to 10 carbon atoms, in particular n-pentane, n-hexane, n-heptane and n-octane.

Examples of halogenated compounds which may be possibly present in the organic solvent are chloroform, trichloroethylene, tetrachloroethylene, tetrachloro-methane, 1,2-dichloroethane, 1,1,1-trichloroethane, 1,1,2-trichloroethane, 1,1,-dichloro-1-fluoroethane (HCFC-141b), 1,1,1- or 1,1,2-trifluorotrichloroethane, 1,2,3-trichloropropane, perfluorinated hydrocarbons, bromobenzene, o-dichlorobenzene, p-chlorotoluene, p-chlorotrifluorobenzene and 1,2-dichloro-4-trifluorobenzene, as well as mixtures of these compounds.

The organic solvent however preferably consists essentially of one or more chloro(fluoro)butanes of general formula (I), 1,1,1,3,3-pentachlorobutane constituting the most preferred organic solvent.

Among the organic solvents containing chloro(fluoro)butanes of general formula (I), those which contain at least one chlorofluorobutane containing 3 or 4 fluorine atoms are preferred. Examples of chlorofluorobutanes of general formula (I), containing 3 or 4 fluorine atoms, which can be used in the organic solvent, are 1,1-dichloro-1,3,3-trifluorobutane (HCFC-363kfc), 3-chloro-1,1,1,3-tetrafluorobutane (HCFC-364mfb) and 1-chloro-1,1,3,3-tetrafluorobutane (HCFC-3641fc). These compounds may be obtained when 1,1,1,3,3-pentachlorobutane is subjected to a hydrofluorination reaction.

In one variant, the organic solvent containing at least one chloro(fluoro)butane of general formula (I) containing 3 or 4 fluorine atoms contains in addition 1,1,1,3,3-pentachlorobutane. It may be advantageous to use mixtures containing 1,1,1,3,3-pentachlorobutane in order to improve the decantation properties during extraction.

Another variant of the process according to the invention relates to a process in which (a) 1,1,1,3,3-pentachlorobutane is subjected to a hydrofluorination reaction (b) a quantity of reaction mixture is drawn off and subjected to a separation operation in order to recover at least one organic solvent comprising chlorofluorobutanes of general formula (I)

(c) the organic solvent is used in the separation process according to the invention.

The separation operation is, for example, a distillation or a demixing at low temperature. The fractions other than the organic solvent may be recycled to the 1,1,1,3,3-pentachlorobutane hydro-fluorination reaction or may be subjected to subsequent separation stages in order to recover 1,1,1,3,3-pentafluorobutane.

In a preferred manner, the extraction is carried out on a mixture comprising HF and HFC-365mfc in proportions close to those in which they form an azeotropic composition. The mixture may in addition comprise variable quantities of a chlorofluorobutane of general formula (I). Often the chlorofluorobutane is a chlorofluorobutane of general formula (I) in which the sum of a and b is equal to 1 or 2.

If the initial mixture of hydrogen fluoride and HFC-365mfc departs from the azeotropic composition, it may be advantageous to carry out beforehand a distillation in order to separate the azeotrope from the compound in excess. The azeotropic composition is then subjected to extraction.

In the separation process according to the invention, the weight ratio between the organic solvent and the mixture of hydrogen fluoride and 1,1,1,3,3-pentafluorobutane is generally at least 0.1. Preferably, a weight ratio of at least 0.2 is used. Generally, the weight ratio between the organic solvent and the mixture of hydrogen fluoride and 1,1,1,3,3-pentafluorobutane does not exceed 10. Preferably, it does not exceed 5.

The temperature at which the extraction is carried out is generally at least −25° C. Preferably, it is about −10° C. The temperature in general does not exceed 40° C. Preferably it does not exceed 30° C.

The process according to the invention is carried out at a sufficient pressure to maintain the mixture in the liquid state. It may be carried out at the autogenous pressure of the mixture; in this case, the pressure is generally less than 3 bar. Alternatively, it may be carried out at a pressure greater than the autogenous pressure. In this case, the total pressure will be generally less than 10 bar; preferably, the pressure used will be less than 3 bar but greater than 1 bar.

The bringing of the mixture of hydrogen fluoride and 1,1,1,3,3-pentafluorobutane into contact with the organic solvent for extraction is carried out in one or more stages, by means of any conventional liquid—liquid extraction device, for example by bringing into intimate contact by means of a static mixer, a stirred reactor, a rotating disc extractor, a centrifugal extractor or a perforated plate column, operating either countercurrentwise or cocurrentwise. Preferably, the bringing into contact is carried out in a stirred reactor. The extraction may be performed continuously or batchwise. Preferably, it is performed continuously.

After extraction, an organic phase enriched in 1,1,1,3,3-pentafluorobutane is separated from a phase enriched in hydrogen fluoride (called hereinafter HF phase). This separation may be simply carried out by decantation, but it can also use any other conventional phase separation device, such as centrifugation or a separation by hydrocyclone. Separation by decantation is preferred.

The organic phase mainly comprises the extraction solvent enriched in 1,1,1,3,3-pentafluorobutane, but it may also contain a certain quantity of hydrogen fluoride. Its composition most often corresponds to the equilibrium composition, determined by the partition coefficients of the various compounds between hydrogen fluoride and the extraction solvent.

1,1,1,3,3-Pentafluorobutane may be easily separated from other constituents of the organic phase by a conventional separation technique such as distillation. 1,1,1,3,3-Pentafluorobutane may then be treated by the wet route in order to remove the last traces of acidity and/or adsorbed onto activated charcoal and/or deacidified on zeolite or alumina. The solvent may be partially or completely recycled to the extraction stage.

When the extraction solvent essentially consists of chloro (fluoro)butanes of general formula (I), it may, after separation of the 1,1,1,3,3-pentafluorobutane extracted, be sent as it is, partially or completely, directly to a reactor for the manufacture of 1,1,1,3,3-pentafluorobutane by hydrofluorination of such chlor(fluoro)butanes of general formula (I), in particular by hydrofluorination of 1,1,1,3,3-pentachlorobutane.

The HF phase contains mainly hydrogen fluoride depleted of 1,1,1,3,3-pentafluorobutane, but may also contain a significant quantity of extraction solvent.

When the extraction solvent essentially consists of chloro (fluoro)butanes of general formula (I), the HF phase may be sent as it is directly to a reactor for the manufacture of 1,1,1,3,3-pentafluorobutane by hydrofluorination of such chloro(fluoro)butanes of general formula (I), in particular by hydrofluorination of 1,1,1,3,3-pentachlorobutane. With solvents containing a compound which is not a precursor of 1,1,1,3,3-pentafluorobutane, such a solution is only possible when this compound is sufficiently inert under the reaction conditions.

The invention also relates to a process for the manufacture of 1,1,1,3,3-pentafluorobutane by hydro-fluorination of chloro(fluoro)butanes of general formula (I), in which chloro(fluoro)butanes of general formula (I) which have served as extraction solvent in the separation process according to the invention are introduced into a reactor for the manufacture of 1,1,1,3,3-pentafluorobutane. In such a manufacturing process, starting material(s) is(are) at least partially supplied to the reactor by used extraction solvent.

In a first variant of the manufacturing process according to the invention, the used extraction solvent is introduced into the hydrofluorination reactor in the form of the HF phase obtained in the separation process according to the invention.

In a second variant of the manufacturing process according to the invention, optionally cumulatively with the first variant above, used extraction solvent is introduced into the hydrofluorination reactor in the form of the organic phase obtained in the separation process according to the invention, from which HFC-365mfc has been essentially separated.

Preferably, the used solvent supplying the hydrofluorination reactor comprises 1,1,1,3,3-pentachlorobutane, advantageously in a content of at least 50% by weight. Preferably, the content of 1,1,1,3,3-pentachlorobutane in the used solvent is at least 80% by weight.

In the process for the manufacture of 1,1,1,3,3-pentafluorobutane according to the invention, it is possible to use known hydrofluorination techniques, in the presence or in the absence of a hydrofluorination catalyst.

The following examples are intended to illustrate the present invention without however limiting the scope thereof.

EXAMPLES 1 to 6

A mixture of 1,1,1,3,3-pentafluorobutane (HFC-365mfc) and of HF close to the azeotropic composition was introduced into a 0.5 l stainless steel (INOX 316) autoclave equipped with a paddle mixer, two dip tubes allowing samples of the two liquid phases to be taken (at the bottom and at the top of the reactor) and a thimble provided with a thermocouple allowing the temperature to be measured, and it was extracted using a solvent. The solvent used and the quantities by weight of HFC-365mfc, of HF and of solvent used are presented in the table below. The autoclave is immersed in a bath maintained at a constant temperature. The extraction is carried out at −10° C. at an autogenous pressure, that is to say slightly less than 1 bar. The mixture was stirred for 1 hour (Example 3, 5 and 6), 4 hours (Ex. 1 and 2) or 24 hours (Ex. 4) and then it was allowed to settle for at least 1 hour.

For each example, the extraction efficiency was evaluated by analysing samples taken from each of the two liquid phases. These liquid samples were taken via a lock chamber of about 5 cm³ after having pressurized the autoclave under 2 bar of nitrogen.

The results of the analysis are presented in the table below.

TABLE

| Ex | Solvent | Starting composition (g) | | | Starting HFC/HF (g/g) | Composition of the organic phase (% by weight) | | | HFC/HF in the organic phase (g/g) |
|---|---|---|---|---|---|---|---|---|---|
|  |  | HFC | HF | Solv. |  | HFC | HF | Solv. |  |
| 1 | Tetrachloroethylene | 130 | 93 | 102 | 1.4 | 11.8 | — | 88.2 | — |
| 2 | Tetrachloroethylene | 101 | 93 | 100 | 1.1 | 9.3 | 0.1 | 90.6 | 93.0 |
| 3 | 1,1,1,3,3-pentachloro-butane | 102 | 106 | 106 | 0.96 | 18.8 | 0.13 | 81.1 | 144.6 |
| 4 | 1,1,1,3,3-pentachloro-butane | 151 | 139 | 42 | 1.08 | 30.1 | 0.5 | 69.3 | 60.2 |
| 5 | 1,1-dichloro-1,3,3-trifluorobutane* | 116 | 113 | 109 | 1.03 | 45.3 | 2.5 | 52.1 | 18.1 |
| 6 | Chlorotetrafluorobutanes/PCBa** | 102 | 119 | 98 | 0.86 | 39.8 | 1.2 | 59.0 | 33.2 |

*technical product consisting of a mixture of C4 products, with a HCFC 363kfc content of 95% by weight
**technical product containing a mixture of C4 products of which 80% by weight of HCFC-364mfb and 12.5% by weight of HCFC-364lfc. The weight ratio between the chlorotetrafluorobutanes and the 1,1,1,3,3-pentachlorobutane (PCBa) in the organic solvent is 0.88.

The results in the table show that the 1,1,1,3,3-pentafluorobutane (HFC–365mfc) concentration in the organic phase is about 9 to 11% by weight when tetrachloroethylene is used as extraction solvent and that it is about 18 to 30% by weight when 1,1,1,3,3-pentachlorobutane is used as extraction solvent. With the mixture of chlorotetrafluorobutanes and 1,1,1,3,3-pentachlorobutane, the 1,1,1,3,3-pentafluorobutane content in the organic phase reaches about 40%. With 1,1-dichloro–1,3,3-trifluorobutane, a 1,1,1,3,3-pentafluorobutane content of about 45% is obtained in the organic phase.

It therefore appears that 1,1,1,3,3-pentachlorobutane extracts roughly twice more HFC–365mfc than tetrachloroethylene while preserving a high HFC–365mfc/HF ratio in the organic phase. Furthermore, the high density of 1,1,1,3,3-pentachlorobutane ensures good properties in relation to the decantation of the phases during the extraction stage. In addition, 1,1,1,3,3-pentachlorobutane does not form an azeotrope with HFC-365mfc which can therefore be easily separated from mixtures with 1,1,1,3,3-pentachlorobutane by distillation.

The use of chlorofluorobutane compounds containing 3 or 4 fluorine atoms (HCFC–363kfc, HCFC–364-mfb, HCFC-364-lfc), pure or as mixtures, makes it possible to further increase the efficiency of extraction of 1,1,1,3,3-pentafluorobutane in the organic phase. 1,1,1,3,3-Pentafluorobutane extraction levels ranging from about 55% to about 71% are obtained. The extraction level indicates the percentage of 1,1,1,3,3-pentafluorobutane extracted in the organic phase compared with the total quantity of 1,1,1,3,3-pentafluorobutane in the starting composition.

The 1,1,1,3,3-pentafluorobutane-free organic phase and the HF phase can be recycled to the reactor for the manufacture of 1,1,1,3,3-pentafluorobutane.

What is claimed is:

1. Process for the separation of hydrogen fluoride from its mixtures with 1,1,1,3,3-pentafluorobutane, according to which the separation is carried out by extraction using an organic solvent containing at least one chloro(fluoro)butane of general formula $CCl_aF_{3-a}CH_2CCl_bF_{2-b}CH_3$, with a an integer from 0 to 3, b an integer from 0 to 2, the sum of a and b being at least equal to 1.

2. Process according to claim 1, in which the organic solvent contains 1,1,1,3,3-pentachlorobutane (a=3 and b=2).

3. Process according to claim 2, in which the organic solvent essentially consists of 1,1,1,3,3-pentachlorobutane.

4. Process according to claim 1, in which the chloro(fluoro)butane contains 3 or 4 fluorine atoms.

5. Process according to claim 4, in which the organic solvent contains, in addition, 1,1,1,3,3-pentachlorobutane.

6. The process according to claim 1, wherein the weight ratio between the organic solvent and the mixture of hydrogen fluoride and hydrofluoroalkane is between 0.1 and 10.

7. The process according to claim 1, wherein the extraction is carried out at a temperature of between −25° C. and 40° C.

8. The process according to claim 1, wherein the extraction is carried out at the autogenous pressure of the mixture.

9. The process according to claim 1, wherein the extraction is carried out at a total pressure of less than 10 bar.

10. The process according to claim 1, wherein the extraction is followed by at least one distillation of the organic phase and/or of the HF phase.

11. The process according to claim 1, in which
(a) 1,1,1,3,3-pentachlorobutane is subjected to a hydrofluorination reaction
(b) a quantity of reaction mixture is drawn off and subjected to a separation operation in order to recover at least one organic solvent comprising chlorofluorobutanes of the formula (I)

(c) the organic solvent is used in the separation process according to claim 1.

12. A process for the manufacture of 1,1,1,3,3-pentafluorobutane by hydrofluorination of chloro(fluoro)butanes of the formula (I),

in which chloro(fluoro)butanes of the formula (I) have served as extraction solvent in the process for the separation of hydrogen fluoride from its mixtures with 1,1,1,3,3-pentafluorobutane according to claim 1, are introduced into a reactor for the manufacture of 1,1,1,3,3-pentafluorobutane.

13. The process according to claim 12, in which used extraction solvent is introduced into the hydrofluorination reactor in the form of the HF phase obtained in the separation process.

* * * * *